(12) United States Patent  
Gunther et al.

(10) Patent No.: US 9,308,262 B2  
(45) Date of Patent: Apr. 12, 2016

(54) PHARMACEUTICAL COMPOSITION FOR ADMINISTRATION TO NAILS

(75) Inventors: Bernhard Gunther, Dossenheim (DE); Bastian Theisinger, Mannheim (DE); Sonja Theisinger, Mannheim (DE)

(73) Assignee: NOVALIQ GMBH, Heidelberg (DE)

( * ) Notice: Subject to any disclaimer, the term of this patent is extended or adjusted under 35 U.S.C. 154(b) by 0 days.

(21) Appl. No.: 14/122,025

(22) PCT Filed: May 24, 2012

(86) PCT No.: PCT/EP2012/059788  
§ 371 (c)(1),  
(2), (4) Date: Nov. 25, 2013

(87) PCT Pub. No.: WO2012/160180  
PCT Pub. Date: Nov. 29, 2012

(65) Prior Publication Data  
US 2014/0140942 A1     May 22, 2014

(30) Foreign Application Priority Data

May 25, 2011  (EP) .................................... 11167552  
May 26, 2011  (EP) .................................... 11167732  
Jul. 19, 2011  (EP) .................................... 11174545

(51) Int. Cl.  
A61K 47/06     (2006.01)  
A61K 31/436    (2006.01)  
A61K 9/70      (2006.01)  
A61K 31/02     (2006.01)  
A61K 31/045    (2006.01)  
A61K 31/192    (2006.01)  
A61K 31/496    (2006.01)

(Continued)

(52) U.S. Cl.  
CPC ............... *A61K 47/06* (2013.01); *A61K 9/7015* (2013.01); *A61K 31/02* (2013.01); *A61K 31/045* (2013.01); *A61K 31/192* (2013.01); *A61K 31/436* (2013.01); *A61K 31/4412* (2013.01); *A61K 31/496* (2013.01); *A61K 31/513* (2013.01); *A61K 31/593* (2013.01)

(58) Field of Classification Search  
None  
See application file for complete search history.

(56) References Cited

U.S. PATENT DOCUMENTS 10,022 A      9/1853   Stockwell  
5,077,036 A   12/1991  Long, Jr.

(Continued)

FOREIGN PATENT DOCUMENTS

EP    0 670 159 A1      9/1995  
EP    0670159 A1 *     9/1995

(Continued)

OTHER PUBLICATIONS

Murdan, Sadaxshina, Enhancing the nail permability of topically applied drugs, Expert opinion Review, Jan. 19, 2009.*

(Continued)

*Primary Examiner* — Robert A Wax  
*Assistant Examiner* — Melissa Mercier  
(74) *Attorney, Agent, or Firm* — Hoxie & Associates LLC (57) ABSTRACT

The invention provides semi-solid or liquid pharmaceutical compositions for topical administration to a finger- or toenail of a human. The compositions are useful for the delivery of active ingredients deep into the nail. Various active ingredients may be incorporated, such as antifungal agents, anti-infectives, anti-inflammatory agents, immunosuppressants, local anesthetics, and retinoids.

13 Claims, 2 Drawing Sheets

(51) Int. Cl.
  *A61K 31/513* (2006.01)
  *A61K 31/593* (2006.01)
  *A61K 31/4412* (2006.01)

(56) References Cited

U.S. PATENT DOCUMENTS

| | | | |
|---|---|---|---|
| 5,326,566 | A | 7/1994 | Parab |
| 5,336,175 | A | 8/1994 | Mames |
| 5,518,731 | A | 5/1996 | Meadows |
| 5,667,809 | A | 9/1997 | Trevino et al. |
| 5,874,469 | A | 2/1999 | Maniar et al. |
| 5,981,607 | A | 11/1999 | Ding et al. |
| 6,042,845 | A | 3/2000 | Sun et al. |
| 6,113,919 | A | 9/2000 | Reiss et al. |
| 6,159,977 | A | 12/2000 | Reeves |
| 6,177,477 | B1 | 1/2001 | George et al. |
| 6,224,887 | B1 | 5/2001 | Samour et al. |
| 6,262,126 | B1 | 7/2001 | Meinert |
| 6,372,243 | B2 | 4/2002 | Kobuch |
| 6,391,879 | B1 | 5/2002 | Reeves |
| 6,458,376 | B1 | 10/2002 | Meadows |
| 6,486,212 | B2 | 11/2002 | Meinert |
| 6,489,367 | B1 | 12/2002 | Meinert |
| 6,730,328 | B2 | 5/2004 | Maskiewicz et al. |
| 7,001,607 | B1 | 2/2006 | Menz et al. |
| 7,258,869 | B1 | 8/2007 | Berry et al. |
| 8,614,178 | B2 | 12/2013 | Theisinger et al. |
| 2002/0128527 | A1 | 9/2002 | Meinert |
| 2003/0018044 | A1 | 1/2003 | Peyman |
| 2003/0027833 | A1 | 2/2003 | Cleary et al. |
| 2004/0266702 | A1 | 12/2004 | Dawson et al. |
| 2005/0079210 | A1 | 4/2005 | Gupta |
| 2010/0008996 | A1 | 1/2010 | Meinert |
| 2010/0226997 | A1 | 9/2010 | Bowman et al. |
| 2010/0274215 | A1 | 10/2010 | Wong et al. |
| 2012/0010280 | A1 | 1/2012 | Aleo et al. |
| 2012/0095097 | A1 | 4/2012 | Tabuchi et al. |
| 2012/0238639 | A1 | 9/2012 | Theisinger et al. |
| 2013/0266652 | A1 | 10/2013 | Theisinger et al. |
| 2013/0303473 | A1 | 11/2013 | Wilson |
| 2014/0004197 | A1 | 1/2014 | Theisinger et al. |

FOREIGN PATENT DOCUMENTS

| | | |
|---|---|---|
| EP | 0 965 329 A1 | 12/1999 |
| EP | 0 965 334 A1 | 12/1999 |
| EP | 0 939 655 B1 | 6/2002 |
| EP | 1 152 749 B1 | 4/2006 |
| EP | 2 110 126 A1 | 10/2009 |
| EP | 2 332 525 A1 | 6/2011 |
| EP | 2 335 735 A1 | 6/2011 |
| EP | 2 462 921 A1 | 6/2012 |
| WO | WO 96/40052 A1 | 12/1996 |
| WO | WO 97/12852 A1 | 4/1997 |
| WO | WO 00/24376 A1 | 5/2000 |
| WO | WO 00/54588 A1 | 9/2000 |
| WO | WO 2005/099718 A1 | 10/2005 |
| WO | WO 2005/123035 A1 | 12/2005 |
| WO | WO 2006/007510 A1 | 1/2006 |
| WO | WO 2007/052288 A2 | 5/2007 |
| WO | WO 2008/060359 A2 | 5/2008 |
| WO | WO 2010/062394 A2 | 6/2010 |
| WO | WO 2011/073134 A1 | 6/2011 |
| WO | WO 2012/052418 A1 | 4/2012 |
| WO | WO 2012/062834 A1 | 5/2012 |
| WO | WO 2012/093113 A1 | 7/2012 |
| WO | WO 2012/160179 A2 | 11/2012 |
| WO | WO 2013/110621 A2 | 8/2013 |
| WO | WO 2014/041055 A1 | 3/2014 |
| WO | WO 2014/041071 A1 | 3/2014 |

OTHER PUBLICATIONS

Murdan, Enhancing the nail permeability of topically applied drugs, Expert Opinion, Drug Delivery (2008) 5(11); 1267-1282.*
Ujiie et al., Sucessful Treatment of Nail Lichen Planus with topical Tacrolimus, Department of Dermatology, Nov. 4, 2009.*
Zakeri et al., Topical calcipotriol therapy in nail psoriasis, A study of 24 cases, Dermatology Online Journal, 2005.*
U.S. Appl. No. 14/122,044, filed Nov. 25, 2013, Theisinger et al.
Ahmed, I. et al., "Disposition of Timolol and Inulin in the Rabbit Eye Following Corneal Versus Non-Corneal Absorption," International Journal of Pharmaceutics, 1987, 38, 9-21.
Chemical Book, 5-Fluorouracil, available at <http://www.chemicalbook.com/ChemicalProductProperty_EN_CB8162744.htm>, accessed Mar. 7, 2014, 1 page.
Davies, N., "Biopharmaceutical Considerations in Topical Ocular Drug Delivery," Clinical and Experimental Pharmacology and Physiology, 2000, 27, 558-562.
Dembinski, R. et al., "Semi-fluorinated Alkanes as Carriers for Drug Targeting in Acute Respiratory Failure," Experimental Lung Research, 2010, 36, 499-507.
Elkeeb, R. et al., "Transungual Drug Delivery: Current Status," International Journal of Pharmaceutics, 2010, 384, 1-8.
Freiburger Dokumentenserver (FreiDok), Albert-Ludwigs-Unversität Freiburg, retrieved from http://www.freidok.uni-freiburg.de/volltexte/5682/, retrieved on Feb. 5, 2014, 2 pages.
Griffin, W., "Classification of Surface-Active Agents by 'HLB'," Journal of the Society of Cosmetic Chemists, 1949, 1, 311-326.
Hardung, H., "Semifluorierte und perfluorierte Verbindungen zur topischen und parenteralen Anwendung," 2008, retrieved from http://www.freidok.uni-freiburg.de/volltexte/5682/pdf/Dissertation_Hardung.pdf.
Hoerauf, H. et al., "Combined Use of Partially Fluorinated Alkanes, Perfluorocarbon Liquids and Silicone Oil: An Experimental Study," Graefe's Archive for Clinical and Experimental Ophthalmology, 2001, 239 (5), 373-381.
International Preliminary Report on Patentability for International Application No. PCT/EP2011/068141 dated Apr. 23, 2013, 4 pages.
International Preliminary Report on Patentability for International Application No. PCT/EP2011/069795 dated May 14, 2013, 8 pages.
International Preliminary Report on Patentability for International Application No. PCT/EP2012/050043 dated Jul. 10, 2013, 5 pages.
International Preliminary Report on Patentability for International Application No. PCT/EP2012/059787 dated Nov. 26, 2013, 9 pages.
International Preliminary Report on Patentability for International Application No. PCT/EP2012/059788 dated Nov. 26, 2013, 8 pages.
International Search Report for International Application No. PCT/EP2011/068141 mailed Dec. 14, 2011, 2 pages.
International Search Report for International Application No. PCT/EP2011/069795 mailed Jan. 16, 2012, 3 pages.
International Search Report for International Application No. PCT/EP2012/050043 mailed Apr. 24, 2012, 2 pages.
International Search Report for International Application No. PCT/EP2012/059787 mailed Dec. 5, 2012, 4 pages.
International Search Report for International Application No. PCT/EP2012/059788 mailed Dec. 3, 2012, 4 pages.
Meinert, H. et al., "The Use of Semifluorinated Alkanes in Blood-Substitutes," Biomaterials, Artificial Cells, and Immobilization Biotechnology, 1993, 21 (5), 583-595.
Meinert, H. et al., "Semifluorinated Alkanes—A New Class of Compounds with Outstanding Properties for Use in Ophthalmology," European Journal of Ophthalmology, 2000, 10 (3), 189-197.
Murdan, S., "Enhancing the Nail Permeability of Topically Applied Drugs," Expert Opinion on Drug Delivery, 2008, 5 (11), 1267-1282.
Pinarci, E. et al., "Intraocular Gas Application in the Diagnosis and Treatment of Valsalva Retiopathy in Case with Premacular Hemorrhage," XP002625604, Retina-Vitreus, 2009, 17 (2), 153-155, abstract only.
Rosca-Casian, O. et al., "Antifungal Activity of *Aloe vera* Leaves," Fitoterapia, 2007, 28, 219-222.
Wong, D. et al., "Perfluorocarbons and Semifluorinated Alkanes," Seminars in Ophthalmology, 2000, 15 (1), 25-35.
Baerdemaeker, L. et al., "Pharmacokinetics in Obese Patients," Continuing Education in Anaesthesia, Critical Care & Pain, 2004, 4, 152-155.

(56) References Cited

OTHER PUBLICATIONS

International Preliminary Report on Patentability dated Mar. 17, 2015, for International Application No. PCT/EP2013/068882, 5 pages.
International Preliminary Report on Patentability dated Mar. 17, 2015, for International Application No. PCT/EP2013/068909, 7 pages.
International Search Report for International Application No. PCT/EP2013/068882 mailed Oct. 30, 2013, 4 pages.
International Search Report for International Application No. PCT/EP2013/068909 mailed Dec. 5, 2013, 4 pages.
U.S. Appl. No. 14/427,927, filed Mar. 12, 2015, Günther et al.
U.S. Appl. No. 14/427,969, filed Mar. 12, 2015, Günther et al.
Gayton, J., "Etiology, Prevalence, and Treatment of Dry Eye Disease," Clinical Ophthalmology, 2009, 3, 405-412.
International Preliminary Report on Patentability for International Application No. PCT/EP2013/051163 dated Jul. 29, 2014, 7 pages.
International Search Report for International Application No. PCT/EP2013/051163 mailed Mar. 4, 2013, 4 pages.
Knepp, V. et al., "Stability of Nonaqueous Suspension Formulations of Plasma Derived Factor IX and Recombinant Human Alpha Interferon at Elevated Temperatures," Pharmaceutical Research, 1998, 15 (7), 1090-1095.
Kociok, N., et al, "Influence on Membrane-Mediated Cell Activation by Vesicles of Silicone Oil or Perfluorohexyloctane," Graefe's Archive for Clinical and Experimental Ophthalmology, 2005, 243, 345-358.
U.S. Appl. No. 14/373,877, filed Jul. 22, 2014, Gunther.
Lemp, M., "Management of Dry Eye Disease," The American Journal of Managed Care, 2008, 14 (3), S88-S101.
Mackiewicz, J. et al., "In Vivo Retinal Tolerance of Various Heavy Silicone Oils," Investigative Ophthalmology & Visual Science, 2007, 48 (4), 1873-1883.
Perry, H., "Dry Eye Disease: Pathophysiology, Classification, and Diagnosis," The American Journal of Managed Care, 2008, 14 (3), S79-S87.
Rosenberg, A., "Effects of Protein Aggregates: An Immunologic Perspective," The AAPS Journal, 2006, 8 (3), E501-E507.
Stevenson, C., "Characterization of Protein and Peptide Stability and Solubility in Non-Aqueous Solvents," Current Pharmaceutical Biotechnology, 2000, 1, 165-182.
Wang, W., "Lyophilization and Development of Solid Protein Pharmaceuticals," International Journal of Pharmaceutics, 2000, 203, 1-60.

* cited by examiner

PHARMACEUTICAL COMPOSITION FOR ADMINISTRATION TO NAILS

CROSS REFERENCE TO RELATED APPLICATIONS

This application is the National Stage Entry under 35 U.S.C. §371 of International Application No. PCT/EP2012/059788 filed May 24, 2012, which claims priority to European Patent Application No. 11167552.6 filed May 25, 2011, European Patent Application No. 11167732.4 filed May 26, 2011, and European Patent Application No. 11174545.1 filed Jul. 19, 2011, the contents of each of which are incorporated herein by reference.

BACKGROUND OF THE INVENTION

The present invention is in the field of pharmacotherapy. More specifically, it relates to the treatment of diseases and conditions affecting the nails of humans and other mammals.

While many cutaneous disorders affect the skin itself, there also exist diseases and conditions which relate to the skin appendages, in particular to the nails. These are often difficult to treat due to the thick and dense nail plate largely composed of keratin and its poor uptake of therapeutic agents.

Nails are hardenings of the horny zone of the epidermis. They appear as sheet-like appendages covering the skin on the dorsal side of the terminal phalanges of fingers and toes. The horny zone of the nail is composed of hard alpha-keratin and has a distal, exposed part, or body, and a proximal, hidden portion, or root. The root is covered by a distal prolongation of the stratum corneum of the skin. This narrow fold is composed of soft-keratin and is termed the eponychium. Distal to the eponychium is the "half-moon," or lunula, a part of the horny zone that is opaque to the underlying capillaries.

Deep to the distal or free border of the nail, the horny zone of the fingertip is thickened and is frequently termed the hyponychium. The horny zone of the nail is attached to the underlying nail bed. The matrix, or proximal part of the bed, produces hard-keratin. Further distally, however, the bed may also generate nail substance. Moreover, the most superficial layer of the nail may be produced by the epithelium immediately dorsal to the root and proximal to the eponychium. The growth of the nail is affected by nutrition, hormones, and disease. Nail growth involves considerable protein synthesis, as a result of which nonspecific changes occur in the nails in response to various local and systemic disturbances.

Nails develop in the fetus as epidermal thickenings that undercut the skin to form folds from which the horny substance of the nail grows distally. In adult humans, it takes about 6 months for a fingernail to form, which corresponds to a growth rate of approx. 2-3 mm per month. Toenails tend to grow more slowly than fingernails.

Nails are about two magnitudes thicker than the stratum corneum of the skin. Hard alpha-keratin, the major constituent of the horny zone, is a fibrous structural protein characterised by a high content of cysteine which readily forms thermostable crosslinks via sulphide bridges. The water content of nails is rather low, and typically ranges from about 10 to 30%. Generally speaking, nails are very resistant to the permeation of molecules such as drug substances.

The main function of nails is to protect the sensitive tips of fingers and toes. In addition, fingernails serve in scratching. Toenails are also important for balance.

One of the most common diseases affecting the nail apparatus is fungal infection, also referred to as onychomycosis, a condition affecting about 20% of the adult population in the USA. The incidence is increasing worldwide. In fact, about 30% of all superficial fungal infections affect the nail. Infection may be due to dermatophyte (ringworm, tinea unguium), yeast, or other non-dermatophyte (mould) species. In paronychia, chronic infection of the nail fold is most often caused by *Candida* species, but bacterial infection with Gram negative species such as *Pseudomonas* may coexist. Acute paronychia (whitlow) due to staphylococcal infection may also occur, and the presence of these bacterial infections will influence management. Invasion of the nail plate by *Candida* species may occur in the presence of paronychia, immune deficiency states (including chronic mucocutaneous candidiasis), Raynaud's disease, or endocrine disorders.

Another common condition is nail psoriasis, one of the possible manifestations of psoriasis, which produces a variety of changes in the appearance of finger and toe nails. These changes include discolouring under the nail plate, pitting of the nails, lines going across the nails, thickening of the skin under the nail, and the loosening (onycholysis) and crumbling of the nail.

Most people who have psoriasis of the nails also have skin psoriasis (cutaneous psoriasis). Only 5% of people with psoriasis of the nails do not have skin psoriasis. In people who have skin psoriasis, 10%-55% have psoriasis of the nails (also called psoriatic nail disease). About 10%-20% of people who have skin psoriasis also have psoriatic arthritis, a specific condition in which people have symptoms of both arthritis and psoriasis. Of people with psoriatic arthritis, 53%-86% have affected nails, often with pitting.

Another condition of the nail is onychia, which is an inflammation of the nail folds surrounding tissue of the nail plate with formation of pus and shedding of the nail. One of the causes of onychia is a posttraumatic bacterial infection.

Onycholysis refers to a loosening of the exposed portion of the nail from the nail bed, usually beginning at the free edge and continuing to the lunula. It may be related to numerous possible causes including infections and allergic reactions.

A number of other nail conditions such as onychodystrophy, onychomadesis, and onychoptosis often represent adverse reactions to drugs, for example antibiotics or anticancer agents.

Interestingly, conditions of the nails are rather often treated systemically, which itself indicates how difficult it is to achieve a therapeutic drug concentration in the nails by local administration. For example, onychomycosis is treated with oral terbinafine 250 mg daily for 3-6 months, or itraconazole 200 mg daily for 3-6 months. Even the rather conventional therapy with oral griseofulvin 10 mg/kg/daily (500 mg twice daily) for 6-18 months is still being recommended today. In particular proximal nail disease or severe nail bed involvement are being considered as indications for systemic rather than local treatment.

Some topical preparations of known antifungal agents for treatment of onychomycosis exist, such as nail lacquers comprising ciclopirox, amorolfine, or butenafine. While there is some evidence of efficacy, it is believed that successful topical antifungal therapy requires treatment over very long periods, such as a year or even more. Some experts recommend the combination of topical and systemic treatment for better efficacy. Without adequate treatment and patient compliance, the infection will not disappear.

Also for nail psoriasis, the most effective treatment options appear to be systemic rather than topical. Recent reports suggest that some injectable biological medicines such as infliximab and etanercept may be highly effective. However, these treatments are associated with substantial risks of adverse effects, and they are very expensive.

Topical treatments in their currently available formulations are considered much less effective. Solutions containing vitamin D derivatives such as calcipotriol may be applied twice daily to the nail folds. Topical high-potency corticosteroid solutions or ointments are another option. Some experts also recommend 5-fluorouracil cream applied to the matrix for 6 months to improve pitting and subungual hyperkeratosis. Antifungal treatment is indicated whenever a secondary fungal infection is present, which is very frequent in cases of nail psoriasis.

There have been various efforts to make topical treatment of nail diseases more successful, mostly focussing on an improved permeation of the drug substance into the nail matrix. Often, co-treatment with urea cream is recommended in order to soften the nail keratin and make it more permeable. While some evidence for an improved antifungal therapy in combination with urea exists, it still appears that systemic therapy with all its risks and adverse effects is considerably more effective.

Other permeation enhancers have been proposed for enhancing trans-nail delivery of antifungal agents, such as in U.S. Pat. No. 6,042,845, U.S. Pat. No. 6,159,977, U.S. Pat. No. 6,224,887 and U.S. Pat. No. 6,391,879. Most of the suggested compounds are however not approved for pharmaceutical products and exhibit unknown health risks.

U.S. Pat. No. 5,326,566 describes a composition of a pharmacological agent in combination with dibutyl adipate, or a mixture of dibutyl adipate and isopropyl myristate, which could enhance the penetration through keratin. However, substantial problems may arise when the penetration enhancers are incompatible with a particular drug substance, leading to drug instability and degradation into potentially harmful degradants.

US 2005/0079210 A1 proposes the use of liposomes the epicutaneous administration of drugs and cosmetically useful agents. However, liposomes are difficult to manufacture cost-effectively and in a reproducible manner.

Other delivery strategies for topical medications require the occlusion of the nail after administration, which is however perceived as inconvenient by many patients.

There clearly remains a need for pharmaceutical formulations and vehicles which allow the effective treatment of nail disorders by topical administration. It is therefore an object of the present invention to provide such improved compositions which overcome one or more disadvantages of known compositions. In particular, it is an object of the invention to provide compositions of topically active drug substances which can effectively penetrate the dense nail plate and which are convenient to use. Further objects of the invention will become clear on the basis of the description of the invention below, including the examples, and of the patent claims.

SUMMARY OF THE INVENTION

The present invention provides a novel pharmaceutical composition for administration to nails. The composition comprises an effective amount of an active ingredient and a semifluorinated alkane (SFA) according to formula RFRH or RFRHRF, wherein RF is a perfluorinated hydrocarbon segment with 20 or less carbon atoms and RH is a non-fluorinated hydrocarbon segment with 3 to 20 carbon atoms. In a preferred embodiment, the SFA is selected from F4H5, F4H6, F4H8, F6H6 and F6H8.

It has been surprisingly found by the inventors that SFAs are capable of delivering active pharmaceutical ingredients effectively into the keratin matrix of finger- and toenails such as to produce therapeutically relevant drug concentrations even in deeper regions of the matrix.

The composition may, for example, be in the form of a solution, gel, nail lacquer, emulsion, suspension, spray, or patch. It is useful for administering a wide range of topical agents useful in various nail diseases and conditions.

DETAILED DESCRIPTION OF THE INVENTION

The invention provides a novel pharmaceutical composition for use as a topical formulation which is to be administered to nails. The composition comprises an effective amount of an active ingredient and a semifluorinated alkane according to formula RFRH or RFRHRF, wherein RF is a perfluorinated hydrocarbon segment with 20 or less carbon atoms and RH is a non-fluorinated hydrocarbon segment with 3 to 20 carbon atoms.

The invention is based on the surprising discovery that the semifluorinated alkanes (SFAs) as defined above are highly suitable carriers for topically administered drugs and capable of delivering active ingredients deep into the nail. This was particularly unexpected in view of Hardung (Doctoral Thesis, Albert-Ludwigs-University of Freiburg, Germany, 2008), who investigated the suitability of SFAs as carriers for topical medications using e.g. testosterone as a model drug, and who came to the conclusion that an SFA such as F6H8 (see below for an explanation of the terminology of SFAs) does not affect an improved penetration, nor interact with the stratum corneum (whose barrier function also relies on keratin), or exhibit any penetration-enhancing effect (p. 103, first full paragraph). However, in spite of such discouraging statements in the prior art, the inventors have further investigated the impact of SFAs and SFA-based carriers on the delivery of drugs into the keratin matrix of nails using excised human nails (in contrast to Hardung who worked with pig skin as a model), and have now surprisingly found that SFAs are indeed capable of enhancing the penetration of drugs into nails, as will be shown in more detail below.

As used herein, a pharmaceutical composition is any composition comprising an active ingredient useful for the diagnosis, prevention, management or therapy of a disease, symptom or health condition and at least one carrier or excipient. A topical formulation is a composition which is in a form suitable for topical administration. In the present invention, the composition is suitable for administration to a skin appendage of a subject, which subject may be a human or an animal. The skin appendage, such as a finger- or toenail, may be intact or injured, bruised, damaged or otherwise affected.

Semifluorinated alkanes are linear or branched alkanes some of whose hydrogen atoms have been replaced by fluorine. In a preferred embodiment, the semifluorinated alkanes (SFA's) used in the present invention are composed of at least one non-fluorinated hydrocarbon segment and at least one perfluorinated hydrocarbon segment. Particularly useful are SFA's which have one non-fluorinated hydrocarbon segment attached to one perfluorinated hydrocarbon segment, according to the general formula $F(CF_2)_n(CH_2)_mH$, or two perfluorinated hydrocarbon segments separated by one non-fluorinated hydrocarbon segment, according to the general formula $F(CF_2)_n(CH_2)_m(CF_2)_oF$.

Another nomenclature which is used herein refers to the above-mentioned SFA's having two or three segments as RFRH and RFRHRF, respectively, wherein $R_F$ designates a perfluorated hydrocarbon segment, $R_H$ designates a non-fluorinated segment. Alternatively, the compounds may be referred to as FnHm and FnHmFo, respectively, wherein F means a perfluorated hydrocarbon segment, H means a non-fluorinated segment, and n, m and o is the number of carbon atoms of the respective segment. For example, F3H3 is used for perfluoropropylpropane. Moreover, this type of nomenclature is usually used for compounds having linear segments. Therefore, unless otherwise indicated, it should be assumed that F3H3 means 1-perfluoropropylpropane, rather than 2-perfluoropropylpropane, 1-perfluoroisopropylpropane or 2-perfluoroisopropylpropane.

Preferably, the semifluorinated alkanes according to the general formulas $F(CF_2)_n(CH_2)_mH$ and $F(CF_2)_n(CH_2)_m(CF_2)_oF$ have segment sizes ranging from 3 to 20 carbon atoms, i.e. n, m and o are independently selected in the range from 3 to 20. SFAs which are useful in the context of the present invention are also described in EP-A 965 334, EP-A 965329 and EP-A 2110126, the disclosure of which documents is incorporated herein.

In a further embodiment, the semifluorinated alkane is a compound according to the formula RFRH, whose segments RF and RH are linear and each—but independently from one another—have from 3 to 20 carbon atoms. In another particular embodiment, the perfluorinated segment is linear and comprises from 4 to 12 carbon atoms, and/or the non-fluorinated segment is linear and comprises from 4 to 8 carbon atoms. Preferred SFA's include in particular the compounds F4H5, F4H6, F4H8, F6H4, F6H6, F6H8, and F6H10. Presently most preferred for carrying out the invention are F4H5, F4H8, F6H6 and F6H8.

Optionally, the composition may comprise more than one SFA. It may be useful to combine SFA's, for example, in order to achieve a particular target property such as a certain density, viscosity, or solubilising capacity for a particular active ingredient. If a mixture of SFA's is used, it is furthermore preferred that the mixture comprises at least one of F4H5, F4H6, F4H8, F6H4, F6H6, F6H8, and F6H10, and in particular one of F4H5, F4H6, F4H8, F6H6 and F6H8. In another embodiment, the mixture comprises at least two members selected from F4H5, F4H6, F4H8, F6H4, F6H6, F6H8, and F6H10, and in particular at least two members selected from F4H5, F6H6, F4H8, and F6H8. Furthermore, mixtures of a semifluorinated alkane, e.g. F4H5, with a perfluorinated compound, such as perfluorooctylbromide or perfluorodecalin, or with another oily material are also contemplated. Other oily materials would, for example, include silicone oils, triglycerides (e.g. native or synthetic medium-chain triglycerides), or compounds such as isopropyl myristate. In some preferred embodiments, however, perfluorinated compounds are absent.

Liquid SFA's are chemically and physiologically inert, colourless and stable. Their typical densities range from 1.1 to 1.7 $g/cm^3$, and their surface tension may be as low as 19 mN/m. SFA's of the RFRH type are insoluble in water but also somewhat amphiphilic, with increasing lipophilicity correlating with an increasing size of the non-fluorinated segment. Again, for practising the current invention, an SFA having a density of at least 1.2 $g/cm^3$ should be selected.

Liquid SFA's of the RFRH type are being used commercially for unfolding and reapplying a retina, for long-term tamponade as vitreous humor substitute (H. Meinert et al., European Journal of Ophthalmology, Vol. 10(3), pp. 189-197, 2000), and as wash-out solutions for residual silicon oil after vitreo-retinal surgery. Experimentally, they have also been used as blood substitutes (H. Meinert et al., Biomaterials, Artificial Cells, and Immobilization Biotechnology, Vol. 21(5), pp. 583-95, 1993). These applications have established SFA's as physiologically well tolerated compounds. On the other hand, SFA's have not been used as excipients in approved drug products as of today.

For allowing convenient administration to the nails, the composition is preferably liquid or semi-solid. As used herein, semi-solid means that a material behaves like a solid upon the exertion of low shear force, but above a certain force threshold, the so-called "yield point", it behaves like a viscous fluid.

Whether liquid or semi-solid, the composition may represent a single phase (i.e. a solution), or consist of two or more phases. A solution may be applied as such, preferably using a brush-like applicator, or it may be sprayed on if the dispenser is adapted to emit the formulation as an aerosol or spray. Optionally, the formulation may contain a film-forming excipient such as a modified cellulose (e.g. nitrocellulose), an acrylic or methacrylic polymer or copolymer, a polyester, poly(butylhydrogen maleate-co-methoxyethylene) or another suitable resin, such as to represent a nail lacquer which is applied as a solution and then dries to form a solid film on the nail. In addition to a film-forming resin, such composition may contain an excipient for improving the adhesion of the film-forming material on the nail, such as a tosylamide-formaldehyde resin. Moreover, it may contain a plasticiser such as triacetin, camphor, a phthalate, triethyl citrate or the like to improve the flexibility of the film and decrease its brittleness. It may also be advantages to incorporate a volatile cosolvent such as ethyl acetate, ethanol, 1-propanol, 2-propanol, or acetone.

In a further embodiment, the composition is in the form of an emulsion. As used herein, an emulsion is a system comprising a dispersed (or inner, or emulsified, or discontinuous) liquid phase within a continuous (or outer, or coherent) liquid or semisolid phase. The two phases are not miscible. In an O/W-emulsion (also referred to as oil-in-water emulsion), a water-immiscible organic liquid phase, which does not have to be an "oil" by any specific definition, is dispersed in a water-miscible continuous phase which may or may not be substantially comprised of water itself.

In another embodiment, the composition is in the form of a microemulsion. A microemulsion is a clear, thermodynamically stable, optically isotropic mixture of a lipophilic component, a hydrophilic component, and an amphiphilic component. Typically, a microemulsion forms spontaneously when the components are combined and mixed with each other, without requiring high energy input as is normally required for the formation of an "ordinary" emulsion. Microemulsions may have a colloidal lipophilic phase dispersed in a hydrophilic phase, or a hydrophilic phase colloidally dispersed in a lipophilic phase. The size of the dispersed phases is usually in the range from about 5 nm to about 400 nm, and most often below about 200 nm. In one of the preferred embodiments of the invention, the particle size is from about 5 nm to about 100 nm. In terms of its rheological properties, the microemulsion may be in the form of a liquid or a gel, i.e. in liquid or semisolid form. In a preferred embodiment, the microemulsion is in liquid form.

For microemulsions according to the invention, it is preferred to use an oil phase comprising from about 5 to about 95 wt.-% of SFA, and more preferably from about 10 to about 80 wt.-% of SFA, the remainder of the oil phase being another oil such as isopropylmyristate. With respect to the incorporation of aqueous components, surfactants and optionally cosurfactants, commonly known constituents of microemulsions may be used to formulate the composition.

It is proposed that emulsions and microemulsions may be particularly suitable to treat proximal regions of nails at their interface to the skin, in particular involving administration to the eponychium, which is the small band of epithelium that extends from the posterior nail wall onto the base of the nail. The eponychium is the end of the proximal fold that folds back upon itself to shed an epidermal layer of skin onto the newly formed nail plate, and therefore it is an important target site for the delivery of active ingredients for improving the health of a nail as it is being formed.

Optionally, the composition may be designed to be administered as a nail patch. For this purpose, a liquid or semisolid formulation may be incorporated in a nonwoven material which is covered and held in place by an adhesive patch. Alternatively, the active ingredient and the SFA may be incorporated in an adhesive matrix layer (drug-in-adhesive design). A further option is to fill a liquid, SFA-based drug formulation in a pouch which is covered and applied to the nail by means of an adhesive patch (liquid reservoir design). In this case, the pouch has a (semi)permeable membrane at the interface to the nail, through which the active ingredient and the SFA is released to the nail.

The composition, whether formulated as a solution, microemulsion or conventional emulsion, suspension, or patch, may contain any further pharmaceutically acceptable ingredients as required or useful in view of the intended application. As mentioned above, an additional solvent or co-solvent may be incorporated, for example in order to achieve a higher solubility for a specific active ingredient, to modify the viscosity or stability of the formulation, or to further enhance the penetration of the active ingredient. Such co-solvent should of course be selected in type, quality and amount such as to maintain the physiological tolerability of the formulation. Potentially suitable co-solvents include ethanol, acetone, ethyl acetate, isopropyl alcohol, glycerol, propylene glycol, pentylene glycol, polyethylene glycol, liquid paraffin, triglyceride oils, hydrofluorocarbons such as HFA 134a and/or HFA 227, and liquid mono- or diglycerides. Among these, ethanol, isopropyl alcohol, and pentylene glycol are among the particularly preferred solvents. It has been found that relatively small amounts of ethanol may substantially modify the solubilising properties of SFAs and allow the incorporation of a number of active ingredients at higher concentrations. For example, the composition may comprise up to about 25 wt.-%, or up to 10 wt.-% of ethanol, or up to about 5 wt.-% of ethanol. Even at a low concentration of up to about 3 wt.-%, ethanol may be a very useful additive in the composition, depending on the specific drug substance to be delivered. Pentylene glycol is also very useful as co-solvent in general and, in particular, it has been found that its incorporation is advantageous in the formulation of microemulsions. Moreover, the composition may comprise one or more stabilisers, surfactants (in particular if the composition is in the form of an emulsion or microemulsion), cosurfactants (in particular if it is in the form of a microemulsion), colouring agents, antioxidants (for example, α-tocopherol), thickeners (viscosity-increasing agents such as bentonite), and fragrances.

If a surfactant is present, it may, for example, be selected from physiologically acceptable phospholipids (such as phosphatidylcholines); nonionic surfactants such as fatty alcohols, pegylated glycerides, pegylated fatty acids, pegylated fatty alcohols, pegylated sorbitan fatty acid esters, and poloxamers; anionic surfactants such as sodium lauryl sulphate, docusate sodium, and sodium deoxycholate.

The composition may be prepared by commonly known techniques for the manufacture of pharmaceutical solutions, emulsions, suspensions, gels, sprays, and microemulsions. Depending on their consistency and specific use, they may be presented in bottles, spray bottles, tubes, with or without applicator.

The active ingredient incorporated within the composition may, in principle, be selected from drug substances which are useful for the prevention, management, or therapy of a disease or condition relating to a nail.

In one of the specific embodiments, the active ingredient is poorly water-soluble. In particular, it water solubility is not more than about 1 mg/mL. In other preferred embodiments, the water solubility is not higher than about 0.1 mg/mL, or not more than about 10 µg/mL, respectively. The invention is particularly useful for delivering such active ingredients because it allows the administration of effective doses in relatively small volumes, which is at least partly due to the surprisingly high solubilisation capacity of semifluorinated alkanes for many poorly water-soluble drug substances.

For the avoidance of doubt, it is affirmed that the invention is not restricted to poorly water-soluble drug substances. It has been found that certain bioactive agents have substantial aqueous solubility, but can also be advantageously formulated in SFA-based carriers.

The active ingredient may be selected from drug substances useful for the prevention and in particular for the management and therapy of any nail disease or condition, or any symptom associated therewith, including nail psoriasis, onychomycosis, onychia, onychocryptosis, onycholysis, onychomadesis, onychoptosis, paronychia, onychomatricoma, anonychia, leukonychia, hapalonychia, erythronychia, nail dystrophy, nail-patella syndrome, as well as pain, itching, and throbbing.

Figure 1:
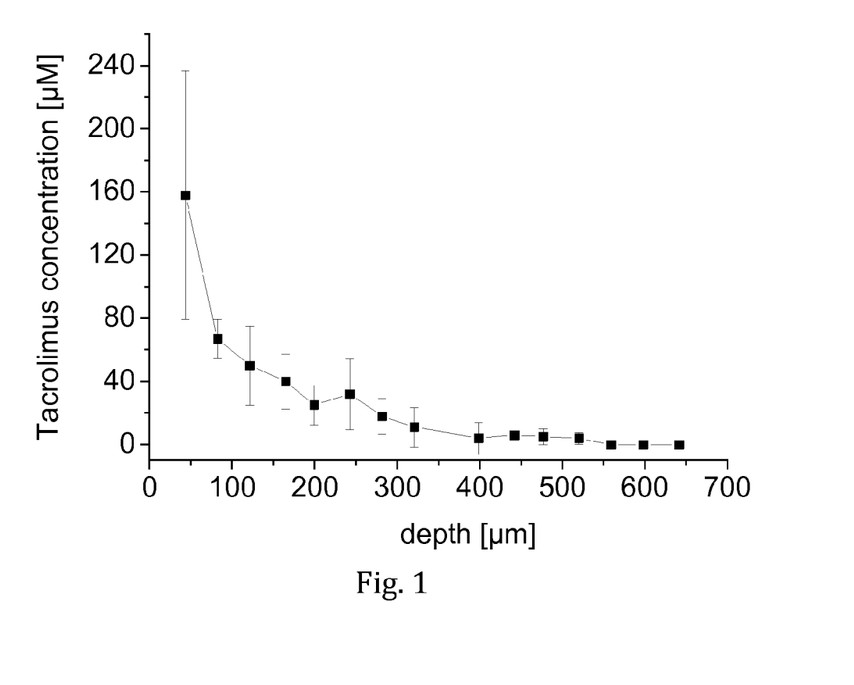
FIG. 1 shows the penetration profile of tacrolimus 1,000 min after administration as an SFA-based formulation to human nails, respectively, presented as molar tacrolimus concentration over depth. For further details, see Example 1.
Figure 2:
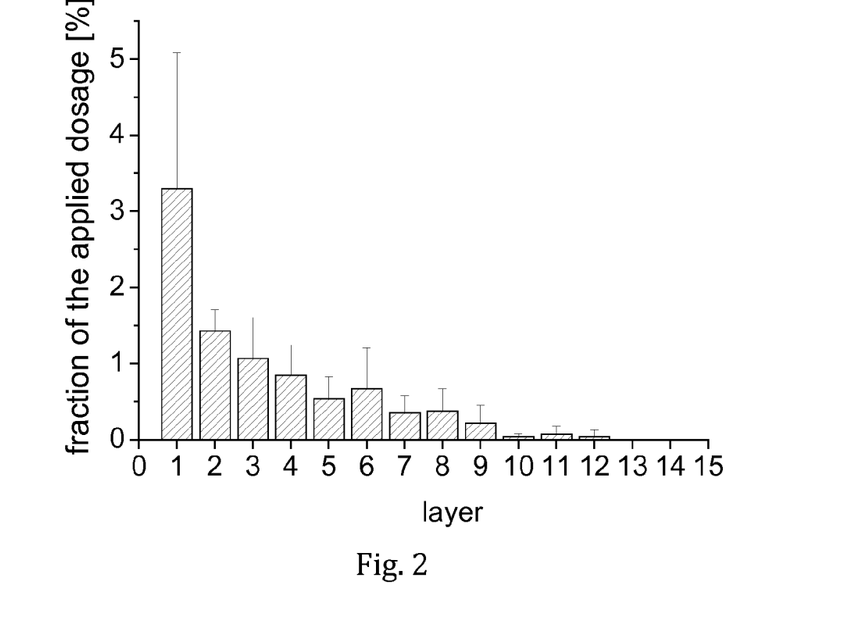
FIG. 2 shows the penetration profile of tacrolimus 1,000 min after administration as an SFA-based formulation to human nails, respectively, presented as amount tacrolimus (relative to the administered dose) per layer. For further details, see Example 1.

In one of the specific embodiments, the composition is used in the therapy of nail psoriasis, and incorporates an active ingredient which may be used to control psoriasis or a symptom thereof. Such active ingredient may, for example, be an immunosuppressant drug, such as a macrolide immunosuppressant. Examples of potentially suitable macrolide immunosuppressants include tacrolimus, sirolimus, everolimus, pimecrolimus, ridaforolimus, temsirolimus, zotarolimus, and ciclosporin A. Tacrolimus is one of the particularly preferred drugs in this group. It has been found by the inventors that tacrolimus can be very effectively (i.e. faster and deeper than using conventional formulations) delivered to the nail matrix. The compound penetrates the nails at least to a depth of 400 µm (see Example 1).

The composition of the invention may enable penetration of therapeutically significant doses of generally poor nail-permeating active ingredients, such as macrolide immunosuppressant, e.g. tacrolimus, into the nail matrix. For example, at least about 8% of the administered dose of active agent may penetrate the nail matrix within 1,000 minutes after topical application of the composition to the nail. In another embodiment, at least about 20 µM of active ingredient may be found at a depth of at least 150 µm, within 1,000 minutes of topical application of the composition to the nail. In a further embodiment, at least about 10 μM of active ingredient may be found at a depth of at least 250 μm, within 1,000 minutes after topical application of the composition to the nail.

Also potentially useful in the treatment of nail psoriasis is the incorporation of an active ingredient from the class of retinoids. Examples of such topically active retinoids include retinol, retinal, tretinoin, isotretinoin, alitretinoin, etretinate, acitretin, tazarotene, bexarotene and adapalene.

Moreover, the incorporation of an active ingredient selected from the class of vitamin D analogues, in particular vitamin D3 analogues, is a further treatment option for nail psoriasis. Examples of these include calcipotriol, calcitriol, and tacalcitol.

Nail psoriasis, but also other conditions of the nail, may involve substantial inflammatory reaction which may be addressed by the incorporation of a corticosteroid or a non-steroidal anti-inflammatory agent (NSAID). Suitable corticosteroid which may be incorporated in an SFA-based composition include amcinonide, betamethasone dipropionate, clobetasol propionate, desonide, desoximetasone, diflorasone diacetate, fluocinolone acetonide, fluocinonide, flurandrenolide, fluticasone propionate, halcinonide, halobetasol proprionate, hydrocortisone, hydrocortisone butyrate, hydrocortisone valerate, mometasone furoate, prednicarbate, and triamcinolone acetonide. Suitable NSAIDs include diclofenac, ibuprofen, ketoprofen, indometacin, piroxicam, flufenamic acid, etofenamate, and flurbiprofen.

Another therapeutic indication in which it is of great importance that the therapeutic agent penetrates the deeper layers of the affected nail is onychomycosis, a fungal infection of the nail. In a particular embodiment, the composition of the invention is for use in the treatment of onychomycosis and comprises an antifungal agent in a therapeutically effective amount or concentration. Antifungal agents which may be incorporated for this purpose include compounds selected from azole antifungals, allylamine antifungals, and others. Proposed for practising the invention are in particular clotrimazole, ketoconazole, miconazole, terbinafine, naftifine, butenafine, ciclopiroxolamine and amorolfine.

The composition of the invention may enable rapid penetration of therapeutically significant doses of active agent, such as an antifungal agent (for example, ciclopiroxolamine). For example, at least about 15% of the administered dose of active agent may have penetrated the nail matrix within 1,000 minutes after topical application of the composition to the nail. In other embodiments, at least about 25%, or at least about 40% of the administered dose of active agent may penetrate the nail matrix within 1,000 minutes after topical application of the composition to the nail.

The composition of the invention may in particular also enable the penetration of the active agent into the deeper layers of the nail. For example, at least about 8% of the administered dose of active agent may penetrate to a depth of at least about 100 μm, within 1,000 minutes after topical application of the composition to the nail. In other embodiments, at least about 3% of the administered dose of active agent may penetrate to a depth of at least about 200 μm, or at least 1% of the administered dose of active agent may penetrate to a depth of at least about 400 μm, within 1,000 minutes after topical application of the composition to the nail.

In a further embodiment, the composition of the invention comprises a local anaesthetic agent such as benzocaine, butamben, dibucaine, lidocaine, oxybuprocaine, bupivacaine, pramoxine, proparacaine, proxymetacaine, and tetracaine. Such composition may be used to relieve pain or itching which may be directly or indirectly caused by various nail diseases and conditions, or which may result from their treatment. Moreover, they may be used in preparation of minor surgical procedures.

Moreover, the composition may comprise an antibiotic agent for use in the prevention or therapy of a bacterial infection. Examples of suitable locally active antibiotics include aminoglycosides such as neomycin or gentamycin; macrolides such as erythromycin and azithromycin; tetracyclins such as chlorotetracyclin, oxytetracyclin, meclocyclin or tetracyclin; and other antibiotics such as retapamulin, clindamycin, fusidic acid, mupirocin, clioquinol, nadifloxacin, or tyrothricin.

The invention is further illustrated by the following examples.

EXAMPLES

Example 1

Tacrolimus was dissolved in a liquid carrier comprising F6H8 and 3.8 wt.-% ethanol to obtain a clear solution having a tacrolimus concentration of 1 mg/mL. The composition was used to evaluate the penetration of tacrolimus from an SFA-based carrier into human nails.

Excised human toe nails were obtained and washed in isotonic sodium chloride solution. For each nail, a filter membrane of 16 mm in diameter (2.01 $cm^2$) was loaded with 30 μL of the test solution, placed onto the nail and incubated for 1,000 min. At the end of the period, the remaining amount of the test solution in the filter and on the nail was collected. From each nail, punch biopsies of 5 mm in diameter (0.1963 $cm^2$) were obtained. The punch biopsies were frozen and microtomised at −40° C. into 20 horizontal slices of 40 μm thickness. Each slice was extracted and analysed for tacrolimus by HPLC-MS, as were the collected amounts of non-permeated formulation.

In result, it was found that tacrolimus was well taken up by the nails during the test period. This is surprising in view of the fact that nails are commonly considered to be very poorly permeable, and that tacrolimus is, due to its molecular size, not a particularly well permeating drug substance. The total amount of tacrolimus found in the nails represented approx. 9% of the administered dose. Significant tacrolimus concentrations were found as deep as 400 μm below the nail surface (see FIG. 1). The respective amounts of the drug in each layer are shown in FIG. 2.

Example 2

The experiment of Example 1 was repeated, except that a solution of ciclopiroxolamine was used instead of a tacrolimus solution. The test composition contained 1% (w/v) of ciclopiroxolamine dissolved in a vehicle of F6H8 and ethanol (85/15 wt.-%).

Figure 3:
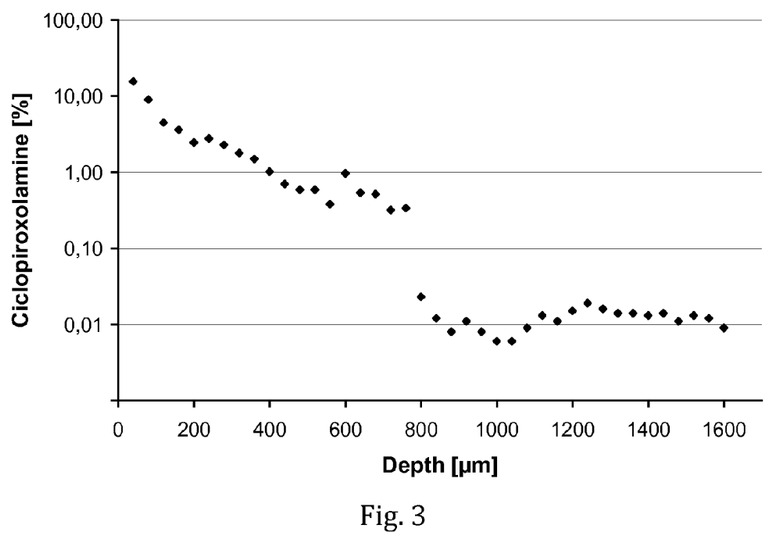
FIG. 3 shows the penetration profile of ciclopiroxolamine 1,000 minutes after administration as an SFA-based formulation to human nails, respectively, presented as amount ciclopiroxolamine (relative to the administered dose) over depth. For further details, see Example 2.

In result, a fraction of 49.5% of the administered amount of ciclopiroxolamine was found in the nail matrix. Even though the compound has a lower molecular weight than tacrolimus, this very high amount of penetrated drug is remarkable and far beyond expectations. Significant amounts of drug were found throughout the depth of the nail matrix (see FIG. 3), indicating the SFAs are an extremely promising vehicle for the delivery of ciclopiroxolamine into nails.

The invention claimed is:

1. A method for the treatment of a disease or condition affecting a nail, comprising administering to the nail a topical pharmaceutical composition comprising
an effective amount of an active ingredient which is (i) an immunosuppressant selected from the group consisting of tacrolimus, sirolimus, everolimus, pimecrolimus, ridaforolimus, temsirolimus, zotarolimus, and ciclosporin A, or (ii) an antifungal agent selected from the group consisting of clotrimazole, ketoconazole, miconazole, terbinafine, naftifine, butenafine, ciclopiroxolamine and amorolfine, and
a semifluorinated alkane according to formula $$RFRH$$

or $$RFRHRF$$

wherein: RF is a perfluorinated hydrocarbon segment with 20 or less carbon atoms, and RH is a non-fluorinated hydrocarbon segment with 3 to 20 carbon atoms.

2. The method of claim 1, wherein the semifluorinated alkane is a compound of formula $$RFRH$$

wherein RF is a linear perfluorinated hydrocarbon segment with 4 to 12 carbon atoms, and wherein RH is a linear alkyl group with 4 to 8 carbon atoms.

3. The method of claim 2, wherein the semifluorinated alkane is selected from F4H5, F4H6, F4H8, F6H6 and F6H8.

4. The method of claim 1, wherein the composition is in the form of a liquid or semisolid solution, gel, spray, emulsion, suspension, microemulsion, nail lacquer, or patch.

5. The method of claim 1, wherein the composition comprises a physiologically acceptable cosolvent selected from ethanol, acetone, ethyl acetate, isopropyl alcohol, glycerol, propylene glycol, pentylene glycol, polyethylene glycol, liquid paraffin, triglyceride oils, hydrofluorocarbons, and liquid mono- or diglycerides.

6. The method of claim 1, wherein the nail is affected by nail psoriasis, and wherein the active ingredient is an immunosuppressant.

7. The method of claim 1, wherein the nail is affected by onychomycosis and wherein the active ingredient is an antifungal agent.

8. The method of claim 1, wherein the nail is a fingernail.

9. The method of claim 1, wherein the nail is a toe-nail.

10. The method of claim 3, wherein the nail is affected by nail psoriasis and wherein the active ingredient is an immunosuppressant.

11. The method of claim 3, wherein the nail is affected by onychomycosis and wherein the active ingredient is an antifungal agent.

12. The method of claim 1 wherein the active ingredient is tacrolimus.

13. The method of claim 1 wherein the active ingredient is ciclopiroxolamine.

* * * * *